US012661003B2

(12) United States Patent
Li et al.

(10) Patent No.: US 12,661,003 B2
(45) Date of Patent: Jun. 23, 2026

(54) QUANTITATIVE MEASUREMENT OF INTRAOCULAR STRUCTURES

(71) Applicant: Duke University, Durham, NC (US)

(72) Inventors: Jianwei Li, Durham, NC (US);
William Raynor, Durham, NC (US);
Joseph Izatt, Durham, NC (US);
Cynthia Toth, Durham, NC (US); **Lejla
Vajzovic, Durham, NC (US); Al-Hafeez
Dhalla, Durham, NC (US); Christian
B. Viehland**, Durham, NC (US)

(73) Assignee: DUKE UNIVERSITY, Durham, NC
(US)

( * ) Notice: Subject to any disclaimer, the term of this
patent is extended or adjusted under 35
U.S.C. 154(b) by 1089 days.

(21) Appl. No.: 17/472,005

(22) Filed: Sep. 10, 2021

(65) Prior Publication Data

US 2022/0079432 A1 Mar. 17, 2022

Related U.S. Application Data

(60) Provisional application No. 63/076,970, filed on Sep.
11, 2020.

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025*
(2013.01); *A61B 3/12* (2013.01); *G06T 7/62*
(2017.01);
(Continued)

(58) Field of Classification Search
CPC ......... A61B 3/102; A61B 3/0025; A61B 3/10;
A61B 3/101; A61B 3/1015; A61B
3/1025;
(Continued)

(56) References Cited

U.S. PATENT DOCUMENTS

2012/0197102 A1* 8/2012 Hanebuchi .............. A61F 2/142
600/398
2015/0168250 A1* 6/2015 Saxer ................. G01B 9/02064
356/479

(Continued)

OTHER PUBLICATIONS

Sun et al. (Intraocular lens alignment from an en face optical
coherence tomography image Purkinje-like method, 2014, Optical
Engineering. 53. 061704. 10.1117/1.OE.53.6.061704) (Year: 2014).*

(Continued)

*Primary Examiner* — Travis S Fissel
(74) *Attorney, Agent, or Firm* — Talem IP Law, LLP

(57) ABSTRACT

A method of imaging intraocular structures, includes cap-
turing, via an optical coherence tomography (OCT) system,
an image of features of an eye, determining geometric
dimensions of elements within the eye from the image,
creating an optical model of the eye with respect to the
intraoperative OCT system using at least one of the deter-
mined geometric dimensions of the elements within the eye
from the image and known dimensions of elements within
the intraoperative OCT system, and applying the optical
model to the image. An OCT system includes an optical
system and a processing system coupled to the optical
system. The processing system includes a processor,
memory, and instructions stored on the memory that when
executed by the processor, direct the intraoperative OCT
system to perform the method of imaging intraocular struc-
tures including creating the optical model and applying the
optical model to the image.

20 Claims, 9 Drawing Sheets

(51) Int. Cl.
| | |
|---|---|
| *A61B 3/12* | (2006.01) |
| *G06T 7/62* | (2017.01) |
| *G06T 12/10* | (2026.01) |
| *G06T 12/30* | (2026.01) |
| *G06V 40/18* | (2022.01) |

(52) U.S. Cl.
CPC .............. *G06T 12/10* (2026.01); *G06T 12/30* (2026.01); *G06V 40/193* (2022.01); *G06T 2207/10101* (2013.01); *G06T 2207/30041* (2013.01)

(58) Field of Classification Search
CPC ....... G06T 7/62; G06T 7/0012; G06T 11/005; G06T 11/008; G06T 2207/10101; G06T 2207/30041; G06T 2207/10072; G06T 2207/10076; G06T 2207/10084; G06T 2207/20172; G06V 40/193
USPC ......................................................... 351/206
See application file for complete search history.

(56) References Cited

U.S. PATENT DOCUMENTS

| | | | |
|---|---|---|---|
| 2016/0249881 A1* | 9/2016 | Aguren | A61B 3/0025 351/216 |
| 2018/0310819 A1* | 11/2018 | Boss | A61B 3/0025 |

OTHER PUBLICATIONS

Estimation of intraocular lens position from full crystalline lens geometry: towards a new generation of intraocular lens (Year: 2018).*

Albert M. Maguire et al. "Age-dependent effects of RPE65 gene therapy for Leber's congenital amaurosis: a phase 1 dose-escalation trial" The Lancet, Oct. 24, 2009, 9 pages, vol. 374.

Steven D. Schwartz et al. "Human embryonic stem cell-derived retinal pigment epithelium in patients with age-related macular degeneration and Stargardt's macular dystrophy: follow-up of two open-label phase 1/2 studies" The Lancet, Oct. 15, 2014, 8 pages, vol. 385.

Richard G. Weleber et al. "Results at 2 Years after Gene Therapy for RPE65-Deficient Leber Congenital Amaurosis and Severe Early-Childhood-Onset Retinal Dystrophy" Ophthalmology, Jul. 2016, 15 pages, vol. 123.

Won Kyung Song et al. "Treatment of Macular Degeneration Using Embryonic Stem Cell-Derived Retinal Pigment Epithelium: Preliminary Results in Asian Patients" Stem Cell Reports, May 12, 2015, 13 pages, vol. 4.

Joseph A. Izatt et al. "Micrometer-Scale Resolution Imaging of the Anterior Eye in Vivo With Optical Coherence Tomography" Archives of Ophthalmology, Dec. 1994, 6 pages, vol. 112.

Yuankai K. Tao et al. "Microscope-integrated intraoperative OCT with electrically tunable focus and heads-up display for imaging of ophthalmic surgical maneuvers" Biomedical Optics Express, May 20, 2014, 9 pages, vol. 5, No. 6.

K. Xue et al. "Technique of retinal gene therapy: delivery of viral vector into the subretinal space" Eye, Aug. 18, 2017, 9 pages, vol. 31.

Nicola G. Ghazi et al. "Treatment of retinitis pigmentosa due to MERTK mutations by ocular subretinal injection of adeno-associated virus gene vector: results of a phase I trial" Human Genetics, 2016, 17 pages, vol. 135.

Bozho Todorich et al. "Impact of Microscope-Integrated OCT on Ophthalmology Resident Performance of Anterior Segment Surgical Maneuvers in Model Eyes" Investigative Ophthalmology & Visual Science, 2016, 8 pages, vol. 57.

S. Tammy Hsu et al. "Volumetric Measurement of Subretinal Blebs Using Microscope-Integrated Optical Coherence Tomography" Translational Vision Science & Technology, Apr. 5, 2018, 11 pages, vol. 7.

Ninel Z. Gregori et al. "Intraoperative Use of Microscope-Integrated Optical Coherence Tomography for Subretinal Gene Therapy Delivery" Retina, The Journal of Retinal and Vitreous Diseases, 2019, 4 pages, vol. 39.

M. Dominik Fischer et al. "Efficacy and Safety of Retinal Gene Therapy Using Adeno-Associated Virus Vector for Patients With Choroideremia: A Randomized Clinical Trial" JAMA Ophthalmology, Aug. 29, 2019, 8 pages, vol. 137.

Peter D. Westenskow et al. "Performing Subretinal Injections in Rodents to Deliver Retinal Pigment Epithelium Cells in Suspension" Journal of Visualized Experiments, Jan. 23, 2015, 6 pages, e52247.

Justis P. Ehlers et al. "Intrasurgical Assessment of Subretinal tPA Injection for Submacular Hemorrhage in the PIONEER study Utilizing Intraoperative OCT" Ophthalmic Surg Lasers Imaging Retina, Mar. 1, 2015, 10 pages, vol. 46.

David Huang et al. "Optical Coherence Tomography" Science, Nov. 22, 1991, 12 pages, vol. 254.

Dan Roberts "Numbers of People with Macular Degeneration and Other Retinal Diseases" Prevent Blindness, Jul. 6, 2013, 6 pages.

Hessam Roodaki et al. "OCT-based volumetric measurement of subretinal injection blebs in ex-vivo porcine eyes" Investigative Ophthalmology & Visual Science, Jun. 2020, 3 pages, vol. 61.

E. A. Swanson et al. "In vivo retinal imaging by optical coherence tomography" Optics Letters, Nov. 1, 1993, 4 pages, vol. 18.

Yuankai K. Tao et al. "Intraoperative spectral domain optical coherence tomography for vitreoretinal surgery" Optics Letters, Oct. 15, 2010, 3 pages, vol. 35.

James Polans et al. "Wide-field optical model of the human eye with asymmetrically tilted and decentered lens that reproduces measured ocular aberrations" Optica, Jan. 30, 2015, 11 pages, vol. 2.

Marisa Zallocchi et al. "EIAV-Based Retinal Gene Therapy in the shaker1 Mouse Model for Usher Syndrome Type 1B: Development of UshStat" PLOS ONE, Apr. 4, 2014, 14 pages, vol. 9.

Kanmin Xue et al. "Beneficial effects on vision in patients undergoing retinal gene therapy for choroideremia" Nature Medicine, Oct. 2018, 10 pages, vol. 24.

Amir H. Kashani et al. "A bioengineered retinal pigment epithelial monolayer for advanced, dry age-related macular degeneration" Science Translational Medicine, Apr. 4, 2018, 11 pages, vol. 10.

O. M. Carrasco-Zevallos et al. "Live volumetric (4D) visualization and guidance of in vivo human ophthalmic surgery with intraoperative optical coherence tomography" Scientific Reports, Aug. 19, 2016, 16 pages, vol. 6.

Knut Stieger et al. "Adeno-Associated Virus Mediated Gene Therapy for Retinal Degenerative Diseases" Adeno-Associated Virus: Methods and Protocols, Methods in Molecular Biology, 2011, 40 pages.

Justis P. Ehlers et al. "Visualization of Real-Time Intraoperative Maneuvers with a Microscope-Mounted Spectral Domain Optical Coherence Tomography System" Retina, The Journal of Retinal and Vitreous Diseases, 2013, 5 pages, vol. 33.

* cited by examiner

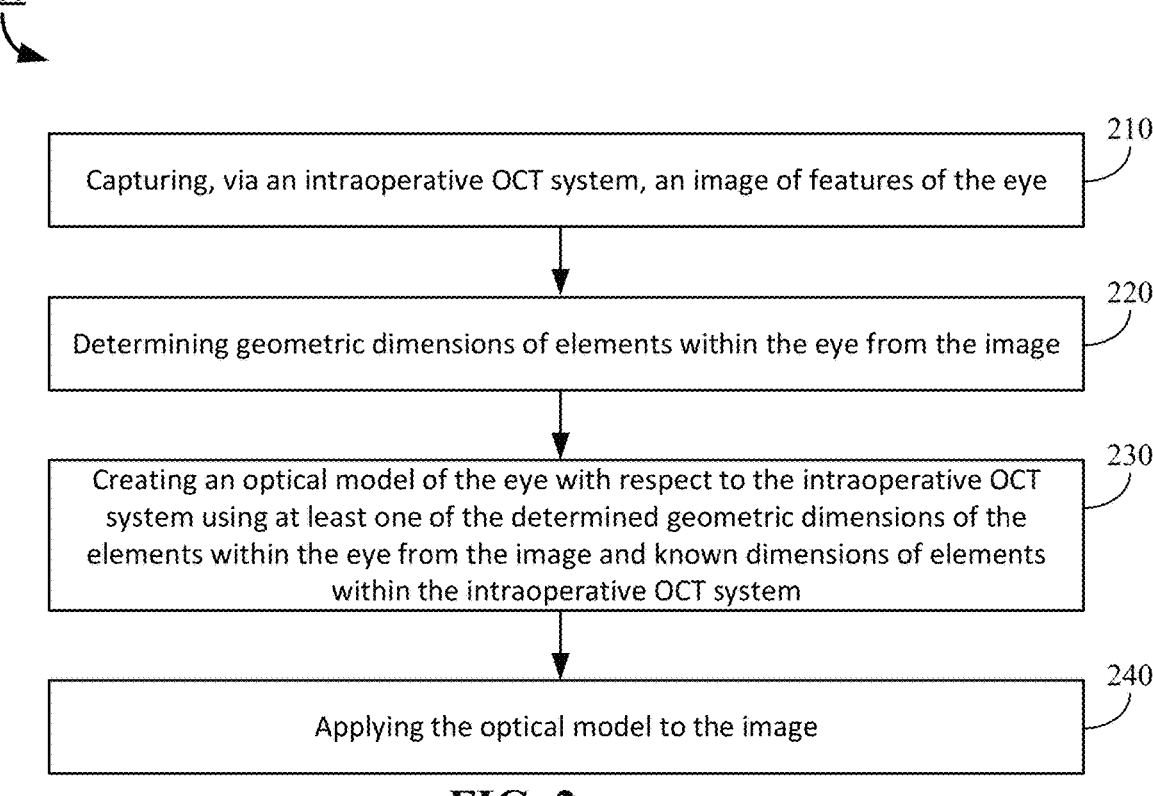

200

210
Capturing, via an intraoperative OCT system, an image of features of the eye 220
Determining geometric dimensions of elements within the eye from the image 230
Creating an optical model of the eye with respect to the intraoperative OCT system using at least one of the determined geometric dimensions of the elements within the eye from the image and known dimensions of elements within the intraoperative OCT system 240
Applying the optical model to the image

FIG. 2

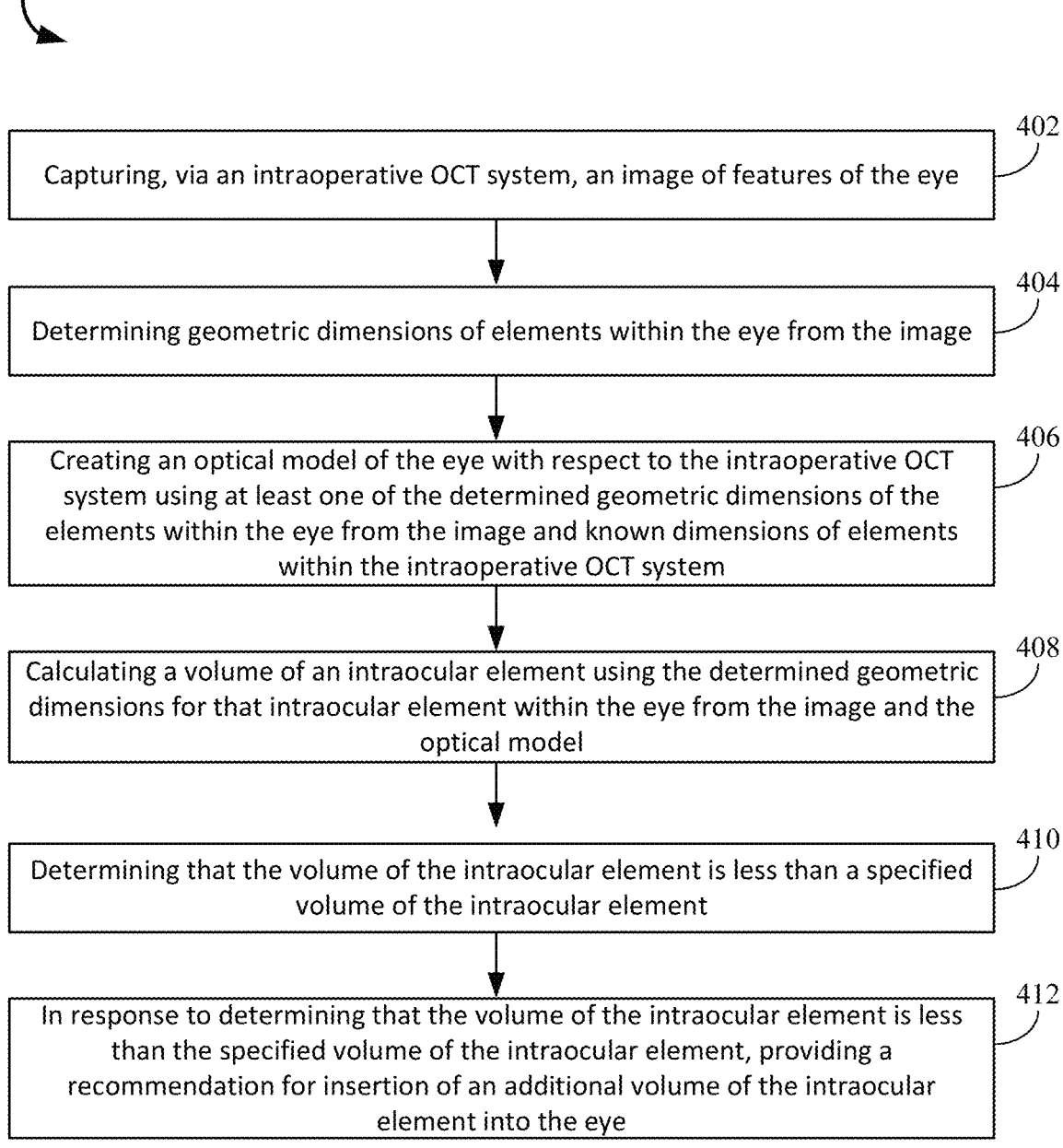

400

402

Capturing, via an intraoperative OCT system, an image of features of the eye

404

Determining geometric dimensions of elements within the eye from the image

406

Creating an optical model of the eye with respect to the intraoperative OCT system using at least one of the determined geometric dimensions of the elements within the eye from the image and known dimensions of elements within the intraoperative OCT system

408

Calculating a volume of an intraocular element using the determined geometric dimensions for that intraocular element within the eye from the image and the optical model

410

Determining that the volume of the intraocular element is less than a specified volume of the intraocular element

412

In response to determining that the volume of the intraocular element is less than the specified volume of the intraocular element, providing a recommendation for insertion of an additional volume of the intraocular element into the eye

FIG. 4A

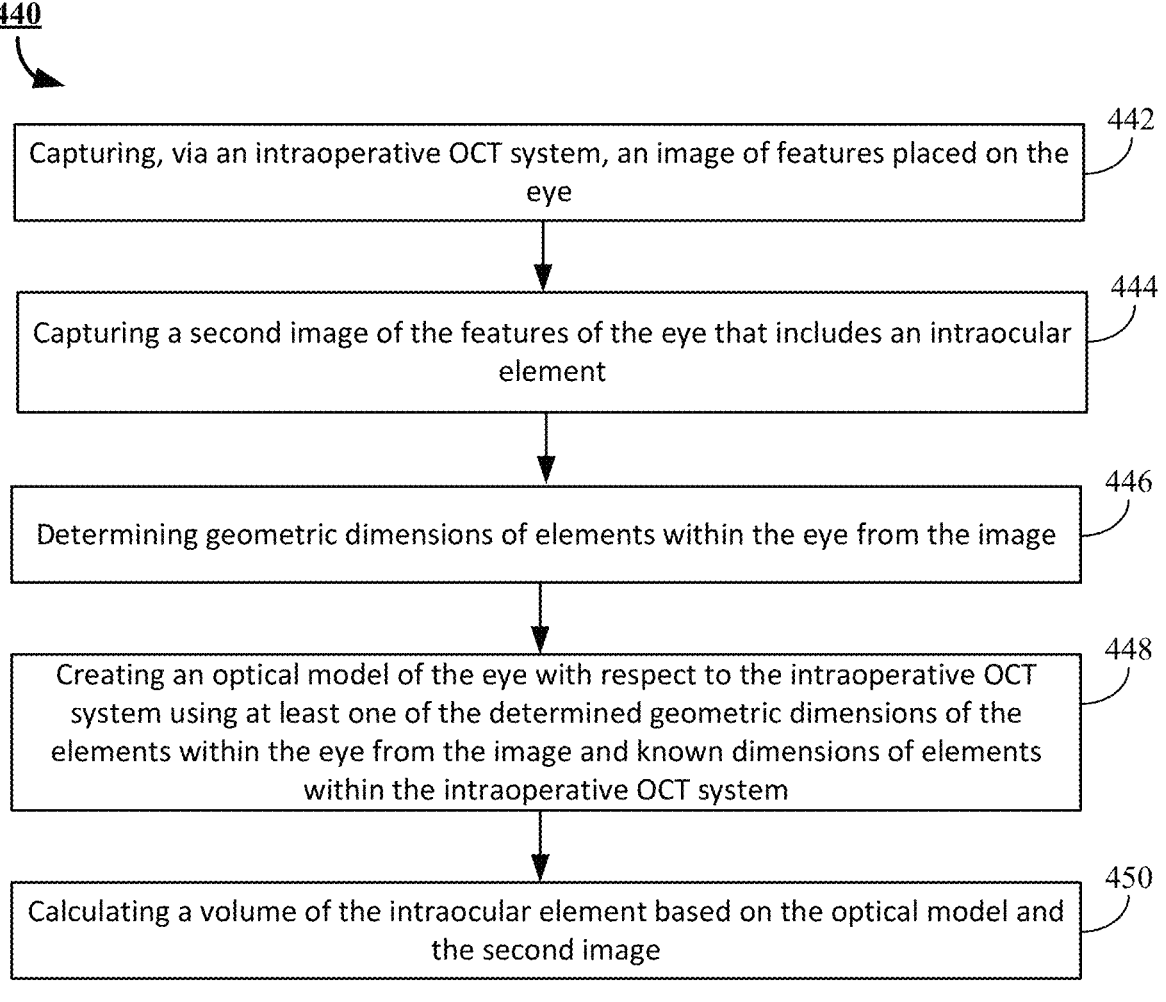

440

Capturing, via an intraoperative OCT system, an image of features placed on the eye — 442

Capturing a second image of the features of the eye that includes an intraocular element — 444

Determining geometric dimensions of elements within the eye from the image — 446

Creating an optical model of the eye with respect to the intraoperative OCT system using at least one of the determined geometric dimensions of the elements within the eye from the image and known dimensions of elements within the intraoperative OCT system — 448

Calculating a volume of the intraocular element based on the optical model and the second image — 450

FIG. 4C

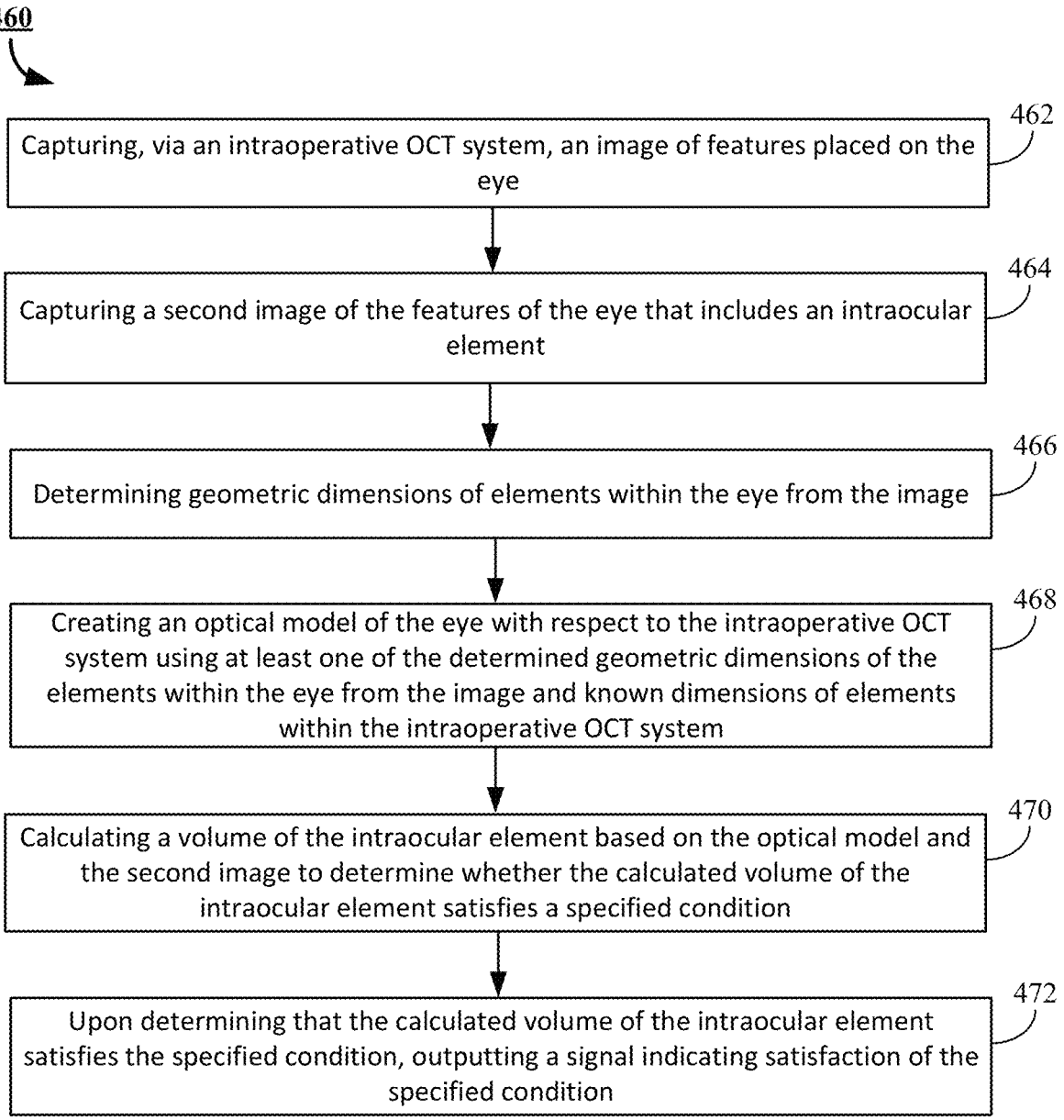

460

Capturing, via an intraoperative OCT system, an image of features placed on the eye — 462

Capturing a second image of the features of the eye that includes an intraocular element — 464

Determining geometric dimensions of elements within the eye from the image — 466

Creating an optical model of the eye with respect to the intraoperative OCT system using at least one of the determined geometric dimensions of the elements within the eye from the image and known dimensions of elements within the intraoperative OCT system — 468

Calculating a volume of the intraocular element based on the optical model and the second image to determine whether the calculated volume of the intraocular element satisfies a specified condition — 470

Upon determining that the calculated volume of the intraocular element satisfies the specified condition, outputting a signal indicating satisfaction of the specified condition — 472

FIG. 4D

QUANTITATIVE MEASUREMENT OF INTRAOCULAR STRUCTURES

STATEMENT REGARDING FEDERALLY SPONSORED RESEARCH

This invention was made with Government support under Federal Grant no. U01EY028079 awarded by the National Institutes of Health National Eye Institute. The Federal Government has certain rights to this invention.

BACKGROUND

Previously untreatable genetic and degenerative retinal diseases such as retinitis pigmentosa, Usher syndrome, Leber's congenital amaurosis, choroideremia, and age-related macular degeneration affects almost one million people in the United States. These debilitating diseases can lead to severe visual impairment and blindness. New therapeutics, including viral vectors, stem cells, and gene therapies, are a promising form of treatment for these diseases. While these treatments show great potential, these injection procedures require complex surgical maneuvers without damaging adjacent structures in and around the eye. Incorrect assessment of the delivered volume and location may lead to suboptimal outcomes or additional complications such as penetration of Bruch's membrane, retinal detachment, or injection into the vitreous cavity. Furthermore, leakage or reflux outside the subretinal space could also lead to suboptimal therapeutic results.

Optical coherence tomography (OCT) allows for imaging of the eye and has become a valuable tool in ophthalmology. OCT systems have also been integrated into surgical optical systems, allowing for real-time imaging of the eye. However, the use of OCT has been limited to qualitative measurements in treating these diseases with injection procedures. Qualitative measurements are useful, but without quantitative measurements, a number of issues can arise, including inaccurate placement and inaccurate volumes of the therapeutics. Indeed, relying on qualitative visual estimation of surgeons to assess delivery success, which can be highly variable depending on the surgeon, may lead to suboptimal outcomes or additional complications described above. Due to these issues, there is a need for qualitative measurements in treating these diseases with injection procedures.

BRIEF SUMMARY

Intraoperative optical coherence tomography (OCT) systems and methods of using those systems are provided. An intraoperative OCT as described herein provides the ability to quantitatively measure a volume and location of an intraocular element within the eye of a patient. For patients with certain diseases (e.g., retinitis pigmentosa, Usher syndrome, Leber's congenital amaurosis, choroideremia, and age-related macular degeneration), treatment by injection of intraocular elements that include therapeutics agents (e.g., viral vectors, stem cells, and gene therapies) can be improved by accurate quantitative data that includes the volume and location of the intraocular element over existing techniques that merely provide qualitative data on the intraocular element injected into the eye of the patient. Indeed, current qualitative techniques do not provide the quantitative data that can be used to prevent suboptimal outcomes or additional complications described currently encountered by injection of intraocular elements.

Advantageously, by including geometric measurements of features of the OCT system itself along with geometric measurements of the eye, a more accurate model of the eye can be created and used to support quantitative measurements of elements in the eye.

A method of imaging intraocular structures includes capturing, via an OCT system, an image of features of an eye, determining geometric dimensions of elements within the eye from the image, creating an optical model of the eye with respect to the intraoperative OCT system using at least one of the determined geometric dimensions of the elements within the eye from the image and known dimensions of elements within the intraoperative OCT system, and applying the optical model to the image.

In some cases, creating the optical model of the eye with respect to the intraoperative OCT system includes adjusting a default model of the eye using the geometric dimensions of the elements within the eye from the image, and using known dimensions of elements within the intraoperative OCT system. In some cases, applying the optical model to the image includes calculating a volume of an intraocular element using the determined geometric dimensions for that intraocular element within the eye from the image and the optical model. In some cases, the method further includes determining that the volume of the intraocular element is less than a specified volume of the intraocular element and in response to determining that the volume of the intraocular element is less than the specified volume of the intraocular element, providing, via a display, a recommendation for insertion of an additional volume of the intraocular element into the eye. In some cases, the intraocular element is a subretinal bleb of a therapeutic agent.

In some cases, the method further includes capturing a second image of the features of the eye, wherein the second image includes an intraocular element and applying the optical model to the image includes calculating a volume of the intraocular element based on the optical model and the second image. In some cases, the intraocular element is not present when the image of the features of the eye is captured before creating the optical model. In some cases, the image of the features of the eye includes an intraocular element and the method further includes determining a location of at least a portion of the intraocular element based on the optical model and the image.

In some cases, the known dimensions of elements within the intraoperative OCT system include a distance related to placement of an optical system of the intraoperative OCT system. In some cases in which the optical system is a contact indirect retinal viewing system, the distance related to the placement of the optical system includes a distance between an initial position of an intermediate image plane of the contact indirect retinal viewing system and a position for imaging a retina of the eye. In some cases in which the optical system is a non-contact indirect retinal viewing system, the distance related to the placement of the optical system includes a distance between an objective of the intraoperative OCT system and a bottom lens of the optical system of the non-contact indirect retinal viewing system. In some cases, the determined geometric dimensions of the elements within the eye from the image comprise an axial eye length.

In some cases, applying the optical model to the image includes determining an additional volume of an intraocular element is needed and the method further includes directing the additional volume of the intraocular element to be inserted into the eye. In some cases, the method further includes capturing a second image of the features of the eye, wherein applying the optical model to the image includes calculating a volume of an intraocular element within the eye based on the optical model and the second image to determine whether the calculated volume of the intraocular element satisfies a specified condition, and upon determining that the calculated volume of the intraocular element satisfies the specified condition, outputting a signal indicating satisfaction of the specified condition. In some cases, the method further includes calibrating the optical model by determining axial and lateral voxel pitches based on the geometric dimensions of the elements within the eye. In some cases, the method further includes visually correcting the image of the features of the eye.

An OCT system for imaging intraocular structures can include an optical system and a processing system coupled to the optical system. The processing system includes a processor, memory, and instructions stored on the memory that when executed by the processor, direct the intraoperative OCT system to capture an image of features of an eye, determine geometric dimensions of elements within the eye from the image, create an optical model of the eye with respect to the intraoperative OCT system using at least one of the determined geometric dimensions of the elements within the eye from the image and known dimensions of elements within the intraoperative OCT system, and apply the optical model to the image.

In some cases, the instructions to create the optical model of the eye with respect to the intraoperative OCT system includes instructions to adjust a default model of the eye using the geometric dimensions of the elements within the eye from the image and use known dimensions of elements within the intraoperative OCT system. In some cases, the instructions to apply the optical model to the image includes instructions to calculate a volume of an intraocular element using the determined geometric dimensions for that intraocular element within the eye from the image and the optical model. In some cases, the instructions further direct the processing system to capture a second image of the features of the eye, wherein the second image includes an intraocular element, and the instructions to apply the optical model include instructions to calculate a volume of the intraocular element based on the optical model and the second image.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 2 illustrates an example method of imaging an intraocular structure for quantitative measurement.

FIGS. 4A-4D illustrate example methods of quantitative measurements of an intraocular element in the eye.

DETAILED DESCRIPTION

Intraoperative optical coherence tomography (OCT) systems and methods of using those systems are provided. An intraoperative OCT as described herein provides the ability to quantitatively measure a volume and location of an intraocular element within the eye of a patient. For patients with certain diseases (e.g., retinitis pigmentosa, Usher syndrome, Leber's congenital amaurosis, choroideremia, and age-related macular degeneration), treatment by injection of intraocular elements that include therapeutics agents (e.g., viral vectors, stem cells, and gene therapies) can be improved by accurate quantitative data that includes the volume and location of the intraocular element over existing techniques that merely provide qualitative data on the intraocular element injected into the eye of the patient. Indeed, current qualitative techniques do not provide the quantitative data that can be used to prevent suboptimal outcomes or additional complications described currently encountered by injection of intraocular elements.

Advantageously, by including geometric measurements of features of the OCT system itself along with geometric measurements of the eye, a more accurate model of the eye can be created and used to support quantitative measurements of elements in the eye.

Figure 1:
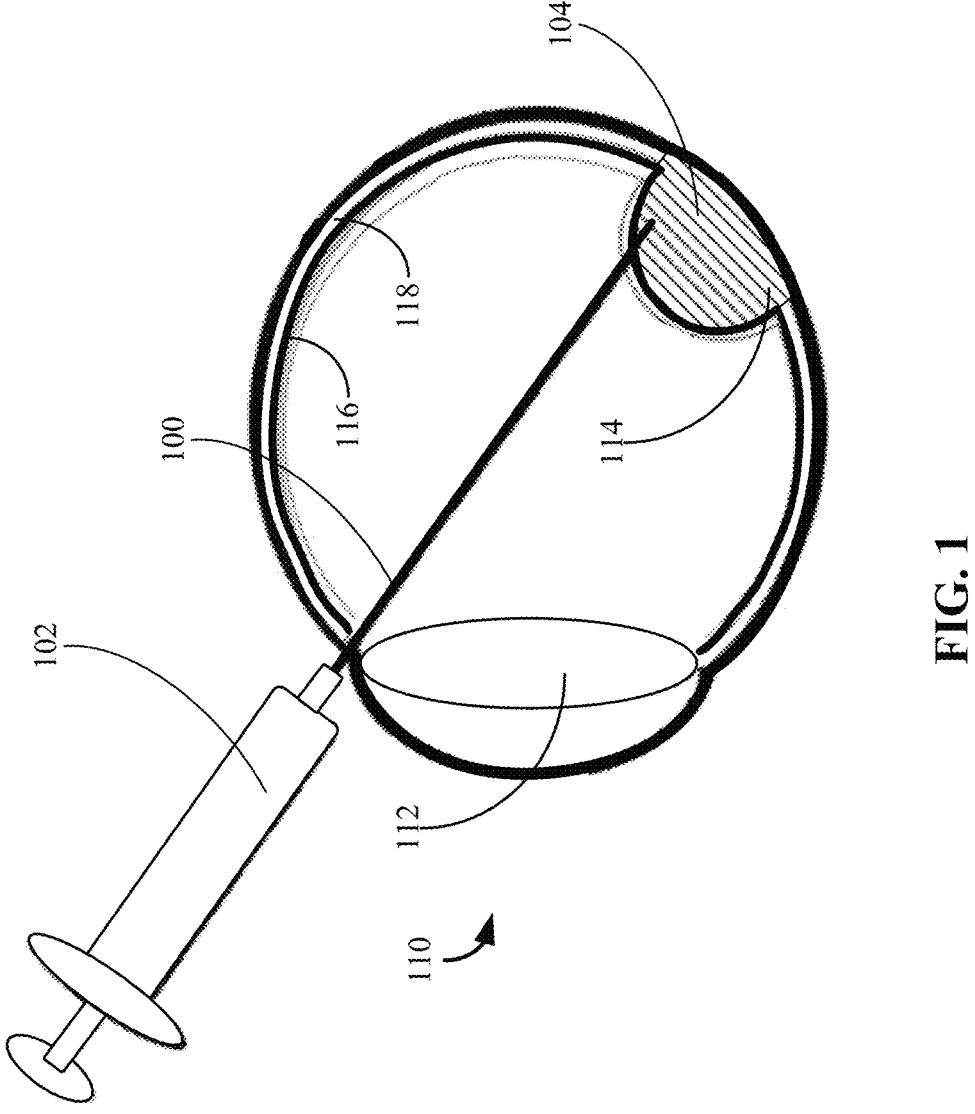
FIG. 1 illustrates an example of an intraocular element being injected into a subretinal region of an eye.

FIG. 1 illustrates an example of an intraocular element being injected into a subretinal region of an eye. Referring to FIG. 1, a needle 100 coupled to a syringe 102 is inserted above a lens 112 an eye 110 of a patient and used to inject an intraocular element 104 into a subretinal space 114 between the retina 116 of the eye 110 and the retinal pigment epithelium (RPE) 118 of the eye 110. Current OCT systems allow for a surgeon so see an image similar to that of FIG. 1, but with no way to actually provide quantitative data on the volume and location of the intraocular element within the eye 110. Advantageously, the intraoperative OCT systems and methods described herein provide the accurate quantitative data that includes the volume and location of the intraocular element within the eye 110 needed to improve outcomes and reduce complications associated with injections of intraocular elements into the eye 110. In some cases, the intraocular element 104 is a subretinal bleb of a therapeutic agent that is injected into the subretinal space 114 between the retina 116 of the eye 110 and the RPE 118 of the eye 110. In some cases, the subretinal bleb may be approximately four times the thickness of the retina 116 and the RPE 118.

FIG. 2 illustrates an example method imaging an intraocular structure for quantitative measurement. Referring to FIG. 2, the method 200 includes capturing (210), via an intraoperative OCT system, an image of features of the eye, determining (220) geometric dimensions of elements within the eye from the image, creating (230) an optical model of the eye with respect to the intraoperative OCT system using at least one of the determined geometric dimensions of the elements within the eye from the image and known dimensions of elements within the intraoperative OCT system, and applying (240) the optical model to the image.

Figure 3:
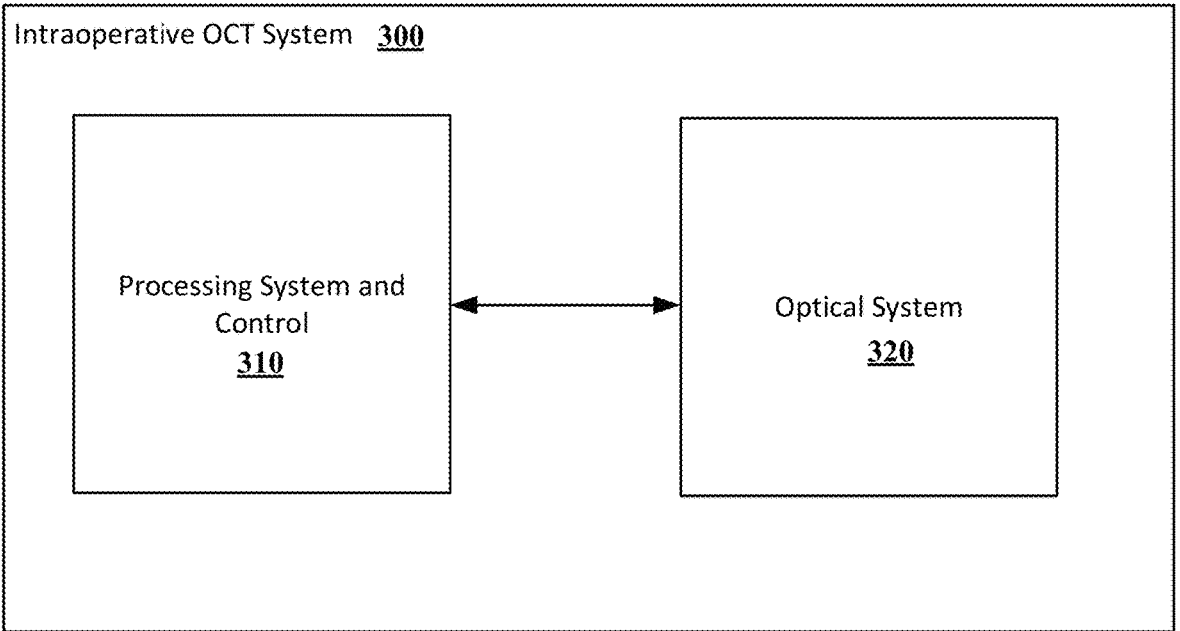
FIG. 3 illustrates a system diagram of an intraoperative OCT system.

FIG. 3 illustrates a system diagram of an intraoperative OCT system. Referring to FIGS. 2 and 3, the method 200 may be carried out via an OCT system 300. The OCT system 300 includes a processing system and control 310 that is in communication with (e.g., coupled to) an optical system 320. In some cases, the processing system and control 310 includes a processor, memory, and instructions stored on the memory that when executed by the processor, direct the intraoperative OCT system 300 to perform the method 200. Specifically, the instructions executed by the processor directs the OCT system 300 to capture (210) an image of features of an eye, determine (220) geometric dimensions of elements within the eye from the image, create (230) an optical model of the eye with respect to the intraoperative OCT system 300 using at least one of the determined geometric dimensions of the elements within the eye from the image and known dimensions of elements within the intraoperative OCT system 300, and apply (240) the optical model to the image. The processing system and control 310 may be implemented in hardware, software, firmware, or combinations of hardware, software, and/or firmware.

An example of the capturing (210) step may include instructions that direct the optical system 320 to direct light to the eye, receive the reflected/backscattered/refracted light at a light detector, and send a signal representing the reflected/backscattered/refracted light to the processing system and control 310. The processing system and control 310 may then create the image from that signal representing the reflected/backscattered/refracted light. It should be understood that this is an example and that any known method of capturing an image of an eye via an OCT system may be utilized for the capturing (210) step.

The determined (220) geometric dimensions of the elements within the eye may be, for example, an axial eye length. The known dimensions of elements within the intraoperative OCT system may be, for example, a distance related to placement of the optical system 320, which is described in further detail with respect to FIGS. 5A, 5B, 6A and 6B. In some cases, the features of the eye may include a cornea, a crystalline lens, a vitreous, a retina, a retinal pigment epithelium (RPE), a Bruch's membrane, a choroid, and/or a sclera. In some cases (e.g., in cases in which more than one image is captured), an image of a thin, flat object placed on top of the eye (e.g., an IR laser viewing card) and/or a spacer lens placed on top of the eye can be captured.

In some cases, creating (230) the optical model of the eye with respect to the intraoperative OCT system 300 includes adjusting a default model of the eye using the geometric dimensions of the elements within the eye from the image and using known dimensions of elements within the intraoperative OCT system 300. The default model of the eye may include an average of geometric dimensions and optical properties within a typical eye. For example, geometric dimensions and optical properties of eyes may be determined from previous patients and a default model may be created from the average geometric dimensions and optical properties of the eyes of those previous patients. In some cases, the default model of the eye may be created using eyes of previous patients who do not have any diseases. In other cases, the default model may be created using eyes of previous patients who have a specific disease(s) that is intended to be treated using the default model of the eye.

In some cases, the method 200 may further include calibrating the optical model by determining axial and lateral voxel pitches based on the determined geometric dimensions of the elements within the eye. This allows for every voxel within the image to be calculated. In some cases, the calibration may include imaging and measuring objects having a known volume within an eye. In some cases, the calibration may be performed prior to the creation (230) of the optical model. In some cases, the method 200 may further include visually correcting the image of the features of the eye.

Figure 4B:
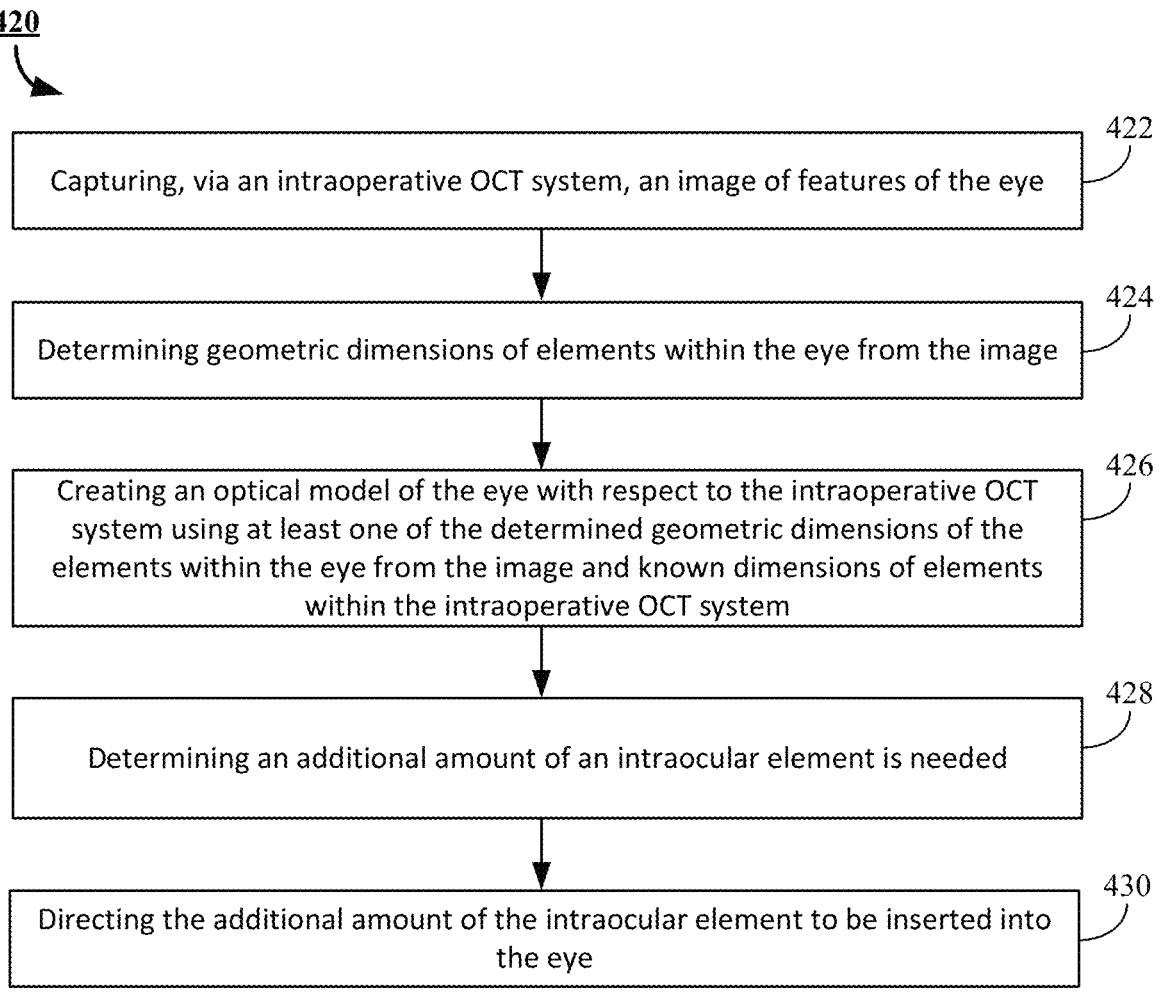

FIGS. 4A-4D illustrate example methods of quantitative measurements of an intraocular element in the eye. Referring to FIGS. 4A and 3, the method 400 may be carried out via an intraoperative OCT system 300. The instructions executed by the processing system and control 310 directs the intraoperative OCT system 300 to capture (402) an image of features of an eye, determine (404) geometric dimensions of elements within the eye from the image, create (406) an optical model of the eye with respect to the intraoperative OCT system 300 using at least one of the determined geometric dimensions of the elements within the eye from the image and known dimensions of elements within the intraoperative OCT system 300, calculate (408) a volume of an intraocular element using the determined geometric dimensions for that intraocular element within the eye from the image and the optical model, determine (410) that the volume of the intraocular element is less than a specified volume of the intraocular element, and in response to determining that the volume of the intraocular element is less than the specified volume of the intraocular element, and provide (412) a recommendation for insertion of an additional volume of the intraocular element into the eye.

The volume of the intraocular element can be calculated (408) by measuring (e.g., from the image) the volume of the intraocular element present within the image. The location of the intraocular element within the eye can be determined in a similar way (e.g., by identifying the intraocular element based on the voxels in the image and measuring distances within the eye with respect to the features of the eye and the intraocular element using the image). In some cases, determining the location of the intraocular element may include determining that at least a portion of the intraocular element is not in a desired location within the eye and/or that at least a portion of the intraocular element is in a desired location within the eye. In some cases, calculating (408) the volume of the intraocular element includes segmenting voxels in the image associated with the intraocular element, calculating a volume for each segmented voxels associated with the intraocular element, and determining a sum of the segmented voxels associated with the intraocular element.

In some cases, the specified volume is predetermined for that patient (e.g., depending on the type and severity of any diseases that patient may have in their eye as well as the size of the eye itself). In some cases, determining (410) that the volume of the intraocular element is less than the specified volume includes comparing (e.g., mathematically) the calculated volume of the intraocular element to the specified volume of the intraocular element. In some cases, the recommendation may be provided (412) via a display that is coupled to and/or in communication with the intraoperative OCT system 300 via a display interface of the intraoperative OCT system 300.

Referring to FIGS. 4B and 3, the method 420 may be carried out via an intraoperative OCT system 300. The instructions executed by the processing system and control 310 directs the intraoperative OCT system 300 to capture (422) an image of features of an eye, determine (424) geometric dimensions of elements within the eye from the image, create (426) an optical model of the eye with respect to the intraoperative OCT system 300 using at least one of the determined geometric dimensions of the elements within the eye from the image and known dimensions of elements within the intraoperative OCT system 300, determine (428) an additional volume of an intraocular element is needed, and direct (430) the additional volume of the intraocular element to be inserted into the eye.

In some cases, determining (428) the additional volume of an intraocular element is needed includes comparing a calculated volume of the intraocular element (and in some cases, a calculated volume of the intraocular element that is in a desired location of the eye) to a specified volume of the intraocular element, and determining the additional volume of the intraocular element that is needed based on that comparison. In some cases, directing (430) the additional volume of the intraocular element to be inserted into the eye includes directing a robot arm (e.g., that is used to inject the intraocular element into the eye) to insert the additional volume of the intraocular element into the eye. In some cases, the robot arm may be coupled to and/or in communication with the intraoperative OCT system via a device interface.

Referring to FIGS. 4C and 3, the method 440 may be carried out via an intraoperative OCT system 300. The instructions executed by the processing system and control 310 directs the intraoperative OCT system 300 to capture (442) an image of features placed on an eye, capture (444) an image of the features of the eye that includes an intraocular element, determine (446) geometric dimensions of elements within the eye from the image of the features of the eye, create (448) an optical model of the eye with respect to the intraoperative OCT system 300 using at least one of the determined geometric dimensions of the elements within the eye from the image of the features of the eye and known dimensions of elements within the intraoperative OCT system 300, including from the image of the features placed on the eye, and calculate (450) a volume of the intraocular element based on the optical model and the image of the features of the eye.

Figures 5A, 5B:
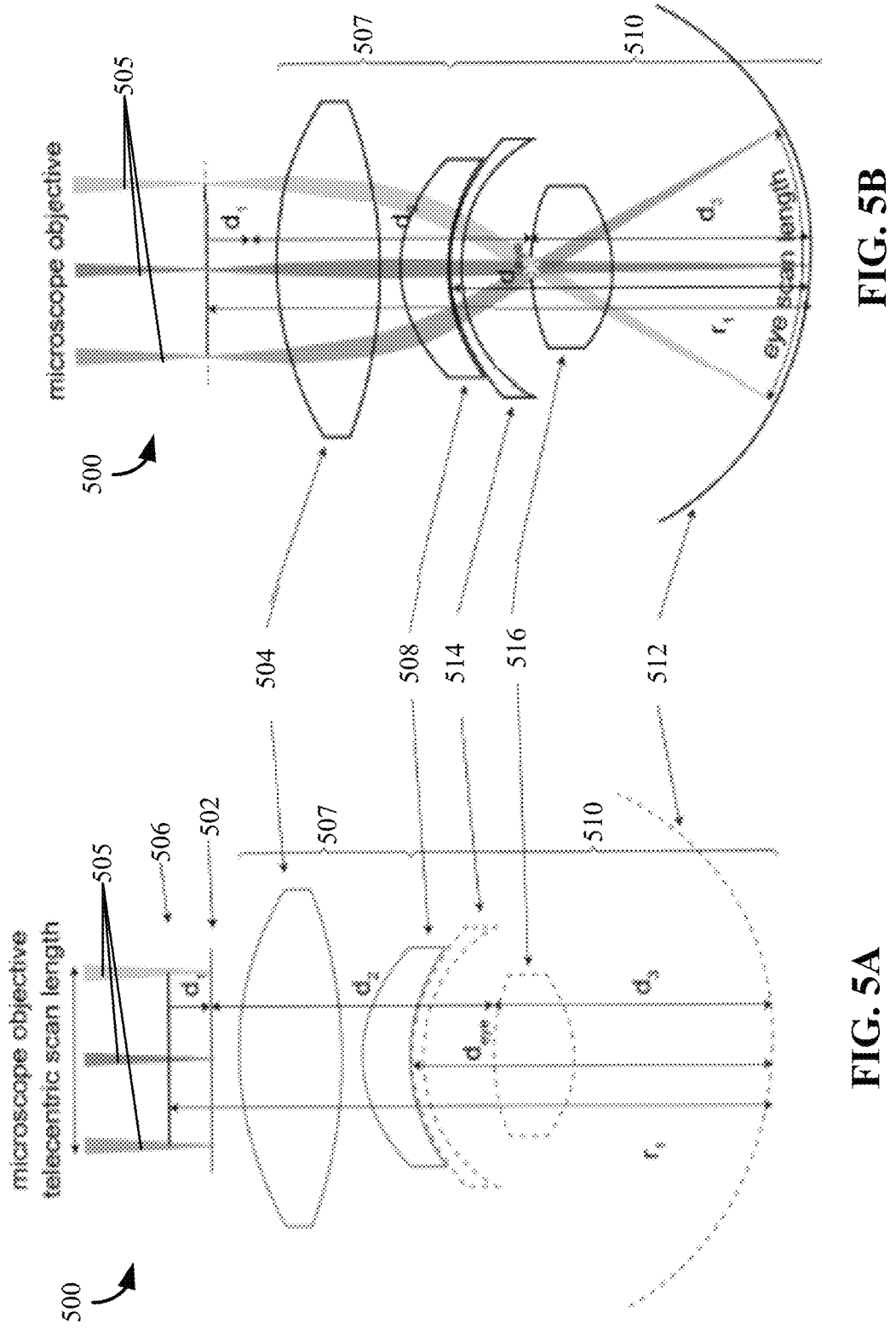
FIGS. 5A and 5B illustrate an example of a contact indirect retinal viewing system.

In some cases, the intraocular element is not present when the image of the features placed on the eye is captured (442) before creating the optical model. That is, the image of the features placed on the eye can be captured before an intraocular element is introduced into the eye. For example, before introducing such an intraocular element into the eye, a feature, such as an IR laser viewing card as described with respect to FIG. 5A, is placed on the eye and an image is captured of that feature to assist with creation of the optical model using known dimensions of elements within the OCT system. In some cases, the intraocular element is not present when the image of the features of the eye is captured (444) before creating the optical model. That is, the image of the features of the eye can be captured before an intraocular element is introduced into the eye and another image (e.g., a third image) is captured that includes the intraocular element before calculating (470) the volume of the intraocular element. In some cases, capturing (442) the image (e.g., a first image) of the features placed on the eye includes imaging a feature, such as an IR laser viewing card as described with respect to FIG. 5A or a spacer lens as described with respect to FIG. 6A, placed on the lens (e.g., 112 of FIG. 1) of the eye. Capturing (444) the image (e.g., a second image or the third image) of the features of the eye that includes the intraocular element may be performed in a manner similar to that of capturing (442) the image of the features of the eye (and as described in further detail above with respect to FIG. 2). In some cases, calculating (450) the volume of the intraocular element within the eye based on the optical model and the image of features of the eye includes measuring (e.g., from the second image) the volume of the intraocular element present within the image of the features of the eye. In some cases, the location of the intraocular element can also be determined by identifying the intraocular element based on the voxels in the image and measuring distances within the eye with respect to the features of the eye and the intraocular element using the image.

Referring to FIGS. 4D and 3, the method 460 may be carried out via an intraoperative OCT system 300. The instructions executed by the processing system and control 310 directs the intraoperative OCT system 300 to capture (462) an image of features placed on an eye, capture (464) an image of the features of the eye that includes an intraocular element, determine (466) geometric dimensions of elements within the eye from the image of the features of the eye, create (468) an optical model of the eye with respect to the intraoperative OCT system 300 using at least one of the determined geometric dimensions of the elements within the eye from the image of the features of the eye and known dimensions of elements within the intraoperative OCT system 300, including from the image of the features placed on the eye, calculate (470) a volume of an intraocular element within the eye based on the optical model and the image of the features of the eye to determine whether the calculated volume of the intraocular element satisfies a specified condition, and upon determining that the calculated volume of the intraocular element satisfies the specified condition, output (472) a signal indicating satisfaction of the specified condition.

Figures 6A, 6B:
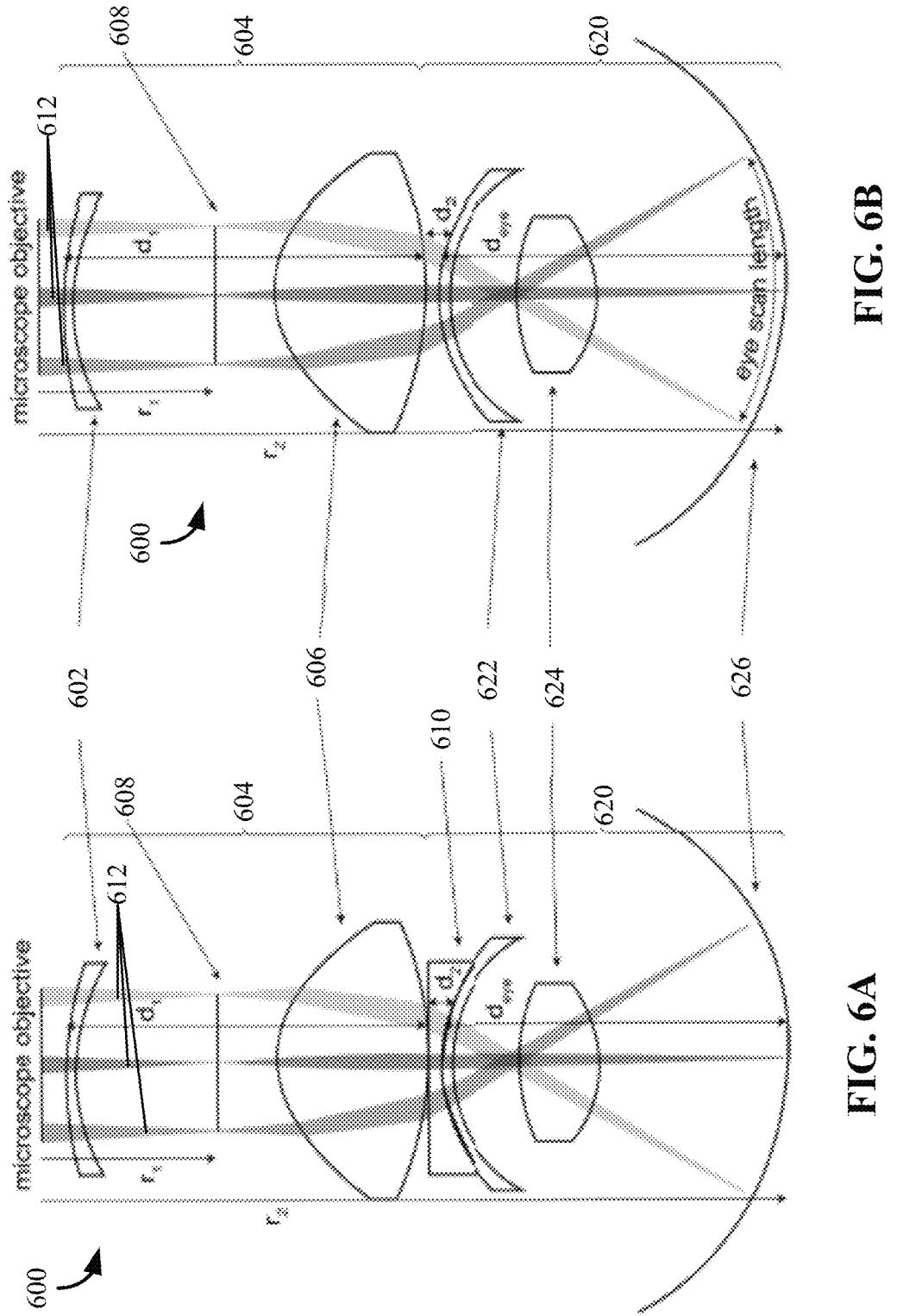
FIGS. 6A and 6B illustrate an example of a non-contact indirect retinal viewing system.

In some cases, capturing (462) the image (e.g., a first image) of the features placed on the eye includes imaging a feature, such as an IR laser viewing card as described with respect to FIG. 5A or a spacer lens as described with respect to FIG. 6A, placed on the lens (e.g., 112 of FIG. 1) of the eye. Capturing (464) the image (e.g., a second image or a third image in cases in which the intraocular element is not present when the second image is captured) of the features of the eye that includes the intraocular element may be performed in a manner similar to that of capturing (462) the image of the features of the eye (and as described in further detail above with respect to FIG. 2). In some cases, calculating (470) the volume of the intraocular element within the eye based on the optical model and the image (e.g., the second image or the third image) of the features of the eye to determine whether the calculated volume of the intraocular element satisfies a specified condition includes segmenting voxels in the image of the features of the eye associated with the intraocular element, calculating a volume for each segmented voxel associated with the intraocular element, determining a sum of the segmented voxels associated with the intraocular element, and determining whether the sum of the segmented voxels associated with the intraocular element is within a range for a desired volume of the intraocular element. In some cases, upon determining that the calculated volume of the intraocular element satisfies the specified condition, outputting (472) a signal indicating satisfaction of the specified condition includes sending a signal to an indicator light and/or display that is coupled to and/or in communication with the intraoperative OCT system 300 via an interface of the intraoperative OCT system. In some cases, upon determining that the calculated volume of the intraocular element satisfies the specified condition, outputting (472) a signal indicating satisfaction of the specified condition includes sending a message (e.g., email, text message, etc.) to an address (e.g., email address, phone number, etc.) via a communication interface of the intraoperative OCT system 300.

In indirect retinal viewing systems, the scanning light is refracted to pivot above the lens, producing chief rays at varying angles and the resulting scan length at the back of the eye is dependent on variables such as the scan length at the intermediate image plane, axial eye length, and a distance related to placement/position of the optical system with respect to the eye. For example, in a longer eye, the scan length increases as the light travels further to reach the retina. To determine accurate quantitative measurements, the values for these variables need to be determined. The scan length at a telecentric image plane can be determined by imaging a microscopy ruler or any other flat surface with
regularly repeating features. However, more complex mea-
surement techniques may be required to determine an axial
eye length and placement/position of the optical system to
create an optical model of the OCT system and the eye.
Using the optical model, locations of individual A-scans and
the scan length to the back of the eye can be used to calculate
the lateral voxel pitch. The axial voxel pitch is dependent on
the laser's imaging depth.

FIGS. 5A and 5B illustrate an example of a contact
indirect retinal viewing system. In a contact indirect viewing
system 500, the bottom lens of the optical system is placed
directly on top of the eye. The geometric dimensions that
need to be determined are the axial eye length ($d_{eye}$) and the
change in distance ($d_1$) of the microscope required to image
the eye 510. In contact indirect viewing systems 500, it is
difficult to measure $d_{eye}$ directly, so an intermediate mea-
surement $d_3$ is used to indirectly measure $d_{eye}$. Referring to
FIG. 5A, a thin, flat object 502 is placed on the top lens 504
of the contact indirect viewing system 500. In some cases,
the thin, flat object 502 is an IR laser viewing card. Light 505
from the intraoperative OCT system is adjusted to focus on
the thin, flat object 502 and the length of the reference arm
($RAP_{IR}$) is noted.

Referring to FIG. 5B, the thin, flat object 502 is removed
and light 505 from the intraoperative OCT system is
adjusted axially to focus on the retina 512 of the eye 510,
and the reference arm position ($RAP_{retina}$) is once again
noted. The difference between the two reference arm lengths
(e.g., $RAP_{retina}$–$RAP_{IR}$) is designated as $r_1$. The distance $d_1$
(e.g., the distance that the microscope moves from the initial
position of the intermediate image plane 506 to a position for
imaging the retina 512) can be determined, for example,
using an external measurement system or via access to
microscope motor position. As an example, a reflection
artifact from the top surface of the contact lens 507 (which
includes the tops lens 504 and the bottom lens 508) can be
used as a fiducial marker in conjunction with the measured
reference arm positions and cavity length of the laser, and $d_1$
can be determined according to the following relationship:

$$d_1=RAP_{retina}+Z_{LA}\times Z_{pitch}-\text{coherence length}-RAP_{IR}+C$$

In this example, $Z_{LA}$ is the axial position of the reflection
artifact, $Z_{pitch}$ is the axial pixel pitch, and C is an example
constant term to account for the distance between the top
contact lens surface and the reference plane. Using these
geometric dimensions, the optical model can be customized
with the geometric dimensions $d_1$ and $d_3$ within the eye 510
for a particular subject. The axial length of the eye ($d_{eye}$) can
then be calculated using a measurable offset from $d_3$.

The distance $d_2$ (e.g., the distance between the reference
plane and the OCT pivot) can be directly measured and is
assumed to be constant. Further assuming the interior cham-
ber of the eye, which includes cornea 514, and the crystalline
lens 516, is constant across subjects, the distance $d_3$ can be
determined according to the following relationship:

$$d_3=r_1-d_2-d_1$$

An optical model can then be customized for that par-
ticular subject can then be created using an image(s) and
information captured by an OCT scan performed by the
intraoperative OCT system. By having geometric dimen-
sional values $d_1$ and $d_{eye}$ embedded in the optical model, a
geometrically dimensionally accurate scale is provided
which can be mapped to the geometric dimensions of the of
elements within the eye from the image. At this point, the optical model can be used to provide quantitative data
including volume, height, location of features within the
eye.

FIGS. 6A and 6B illustrate an example of a non-contact
indirect retinal viewing system. In non-contact indirect
retinal viewing system 600, a ruler (or other distance mea-
surement device) can be used to determine $d_1$, which in this
case refers to a distance between a top lens 602 of a
binocular indirect ophthalmomicroscope (BIOM) lens 604
and a bottom lens 606 of the BIOM lens 604 (which also
includes the intermediate image plane 608).

Referring to FIG. 6A, to determine $d_2$, a spacer lens 610
having a known thickness is placed on top of the eye 620
(which includes the cornea 622, crystalline lens 624, and the
retina 626). The bottom lens 606 of the BIOM lens 604 is
then lowered to contact the spacer lens 610 and the distance
that the bottom lens 606 of the BIOM lens 604 is lowered to
contact the spacer lens 610 is recorded.

Referring to FIG. 6B, the spacer lens 610 is then removed
and the bottom lens 606 of the BIOM lens 604 is restored to
its previous position. Light 612 from the intraoperative OCT
system is adjusted axially to focus on the retina 626 of the
eye 620. By utilizing the difference in reference arm posi-
tions between the intermediate image plane 608 ($RAP_{IIP}$)
and the retina 626 ($RAP_{retina}$) (e.g., in a similar way as
described above with respect to FIG. 5A), the axial eye
length ($d_{eye}$) can be determined to customize the optical
model with geometric dimensions within the eye 620 for that
subject.

Using any of the intraoperative OCT systems described
herein, an example of determining/calculating a volume of
an intraocular element (or any other structure within the eye)
may include generating an optical model from the captured
image(s) and the determined geometric dimensions for that
particular intraoperative OCT system and then using the
generated optical model and the image(s) to calculate lateral
voxel pitches (e.g., X-axis and Y-axis voxel pitches) and the
axial voxel pitch (e.g., the Z-axis voxel pitch). In some
cases, an intraocular element or any other region of interest
can be further processed to provide additional diagnostic
and/or quantitative data. For example, the image(s) can be
segmented using conventional analysis or customized soft-
ware, such as Duke Optical Coherence Tomography Retinal
Analysis Program (DOCTRAP) or Avizo (Thermo Fisher
Scientific, Inc.).

"Approximately" is used to provide flexibility to a
numerical range endpoint by providing that a given value
may be "slightly above" or "slightly below" the endpoint
without affecting the desired result.

As used herein, the term "subject" and "patient" are used
interchangeably and refer to both human and nonhuman
animals. The term "nonhuman animals" includes all verte-
brates (e.g., mammals and nonmammals), such as nonhuman
primates, sheep, dogs, cats, horses, cows, chickens, amphib-
ians, reptiles, and the like.

Although the subject matter has been described in lan-
guage specific to structural features and/or acts, it is to be
understood that the subject matter defined in the appended
claims is not necessarily limited to the specific features or
acts described above. Rather, the specific features and acts
described above are disclosed as examples of implementing
the claims and other equivalent features and acts are
intended to be within the scope of the claims.

What is claimed is:
1. A method of imaging intraocular structures, compris-
ing:

capturing, using an intraoperative optical coherence tomography (OCT) system, an OCT image of features of an eye and intraocular elements introduced to the eye;

determining geometric dimensions of the features of the eye from the OCT image;

determining geometric dimensions of the intraocular elements from the OCT image, wherein the intraocular elements comprise a subretinal bleb of a therapeutic agent;

creating an optical model of the eye with respect to the intraoperative OCT system using at least one of the determined geometric dimensions of the features of the eye from the OCT image and known dimensions of elements within the intraoperative OCT system; and applying the optical model to the OCT image.

2. The method of claim 1, wherein creating the optical model of the eye with respect to the intraoperative OCT system comprises:

adjusting a default model of the eye using the geometric dimensions of the elements within the eye from the OCT image; and using known dimensions of elements within the intraoperative OCT system.

3. The method of claim 1, wherein applying the optical model to the OCT image comprises calculating a volume of an intraocular element using the determined geometric dimensions for that intraocular element within the eye from the OCT image and the optical model.

4. The method of claim 3, further comprising:

determining that the volume of the intraocular element is less than a specified volume of the intraocular element; and in response to determining that the volume of the intraocular element is less than the specified volume of the intraocular element, providing, via a display, a recommendation for insertion of an additional volume of the intraocular element into the eye.

5. The method of claim 1, further comprising:

capturing a second image of the features of the eye, wherein the second image includes an intraocular element;

wherein applying the optical model to the image comprises calculating a volume of the intraocular element based on the optical model and the second image.

6. The method of claim 5, wherein the intraocular element is not present when the image of the features of the eye is captured before creating the optical model.

7. The method of claim 1, wherein the image of the features of the eye includes an intraocular element, the method further comprising determining a location of at least a portion of the intraocular element based on the optical model and the OCT image.

8. The method of claim 1, wherein the known dimensions of elements within the intraoperative OCT system comprise a distance related to placement of an optical system of the intraoperative OCT system.

9. The method of claim 8, wherein the optical system is a contact indirect retinal viewing system, wherein the distance related to the placement of the optical system comprises a distance between an initial position of an intermediate image plane of the contact indirect retinal viewing system and a position for imaging a retina of the eye.

10. The method of claim 8, wherein the optical system is a non-contact indirect retinal viewing system, wherein the distance related to the placement of the optical system comprises a distance between an objective of the intraoperative OCT system and a bottom lens of the optical system of the non-contact indirect retinal viewing system.

11. The method of claim 1, wherein the determined geometric dimensions of the elements within the eye from the OCT image comprise an axial eye length.

12. The method of claim 1, wherein applying the optical model to the OCT image comprises determining an additional volume of an intraocular element is needed;

wherein the method further comprises directing the additional volume of the intraocular element to be inserted into the eye.

13. The method of claim 1, further comprising:

capturing a second image of the features of the eye, wherein the second image comprises an intraocular element;

wherein applying the optical model to the OCT image comprises calculating a volume of an intraocular element within the eye based on the optical model and the second image to determine whether the calculated volume of the intraocular element satisfies a specified condition; and upon determining that the calculated volume of the intraocular element satisfies the specified condition, outputting a signal indicating satisfaction of the specified condition.

14. The method of claim 1, further comprising calibrating the optical model by determining axial and lateral voxel pitches based on the geometric dimensions of the elements within the eye.

15. The method of claim 1, further comprising visually correcting the OCT image of the features of the eye.

16. An intraoperative optical coherence tomography (OCT) system for imaging intraocular structures, comprising:

an optical system; and a processing system coupled to the optical system, the processing system comprises a processor, memory, and instructions stored on the memory that when executed by the processor, direct the intraoperative OCT system to:

capture an OCT image of features of an eye and intraocular elements introduced to the eye, wherein the intraocular elements comprise a subretinal bleb of a therapeutic agent;

determine geometric dimensions of the features of the eye from the OCT image;

determine geometric dimensions of the intraocular elements from the OCT image;

create an optical model of the eye with respect to the intraoperative OCT system using at least one of the determined geometric dimensions of the features of the eye from the OCT image and known dimensions of elements within the intraoperative OCT system; and apply the optical model to the OCT image.

17. The intraoperative OCT system of claim 16, wherein the instructions to create the optical model of the eye with respect to the intraoperative OCT system comprises instructions to:

adjust a default model of the eye using the geometric dimensions of the elements within the eye from the image; and use known dimensions of elements within the intraoperative OCT system.

18. The intraoperative OCT system of claim 16, wherein the instructions to apply the optical model to the OCT image comprises instructions to calculate a volume of an intraocular element using the determined geometric dimensions for that intraocular element within the eye from the OCT image and the optical model.

19. The intraoperative OCT system of claim 16, wherein the instructions further direct the processing system to:

capture a second image of the features of the eye, wherein the second image includes an intraocular element;

wherein the instructions to apply the optical model comprise instructions to calculate a volume of the intraocular element based on the optical model and the second image.

20. The method of claim 1, wherein the subretinal bleb of the therapeutic agent is in a subretinal space between a retina of the eye and a retinal pigment epithelium of the eye.

* * * * *